United States Patent [19]
Matsutani et al.

[11] Patent Number: 5,181,645
[45] Date of Patent: Jan. 26, 1993

[54] MEDICAL STAPLER

[75] Inventors: Kanji Matsutani, Takanezawa; Masatoshi Fukuda, Utsunomiya; Katsutoshi Sato, Kamikawachi, all of Japan

[73] Assignee: Matsutani Seisakusho Co., Ltd., Tochigi, Japan

[21] Appl. No.: 824,152

[22] Filed: Jan. 22, 1992

[30] Foreign Application Priority Data

Jan. 24, 1991 [JP] Japan .................................. 3-22702

[51] Int. Cl.⁵ .......................................... A61B 17/068
[52] U.S. Cl. ...................................... 227/177; 227/19
[58] Field of Search .................. 227/19, 175, 176, 177

[56] References Cited

U.S. PATENT DOCUMENTS

| | | | |
|---|---|---|---|
| 4,261,244 | 4/1981 | Becht et al. | |
| 4,411,378 | 10/1983 | Warman | 227/19 |
| 4,582,237 | 4/1986 | Storace et al. | 227/19 |
| 4,619,262 | 10/1986 | Taylor | 227/19 X |
| 4,619,391 | 10/1986 | Sharkany et al. | 227/19 |
| 4,662,555 | 5/1987 | Thornton | 227/19 |
| 4,747,531 | 5/1988 | Brinkerhoff et al. | 227/19 |
| 4,796,793 | 1/1989 | Smith et al. | 227/19 |
| 4,874,122 | 10/1989 | Froelich et al. | 227/19 |
| 4,919,320 | 4/1990 | Storace | 227/19 |
| 5,022,579 | 6/1991 | Matsutani et al. | 227/129 X |

Primary Examiner—Douglas D. Watts
Assistant Examiner—Rinaldi Rada
Attorney, Agent, or Firm—Wegner, Cantor, Mueller & Player

[57] ABSTRACT

In a medical stapler, an anvil is disposed in the vicinity of an opening in a casing, and is disposed in a path of movement of a ram. A foremost staple placed on the anvil is shaped through the cooperation of the advancing ram with the anvil in such a manner that a pair of legs of this foremost staple are moved toward each other. The anvil has a shaping surface disposed in opposed relation to the ram. This shaping surface is inclined relative to the path of movement of the ram in such a manner as to approach the ram progressively toward the distal end of the shaping surface.

3 Claims, 3 Drawing Sheets

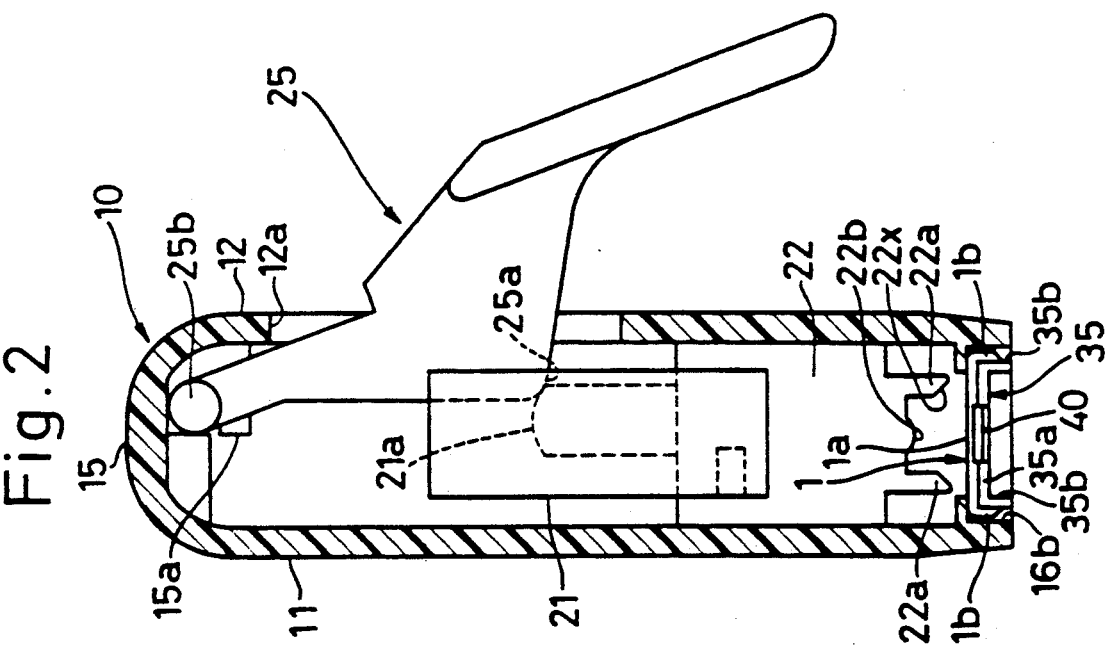
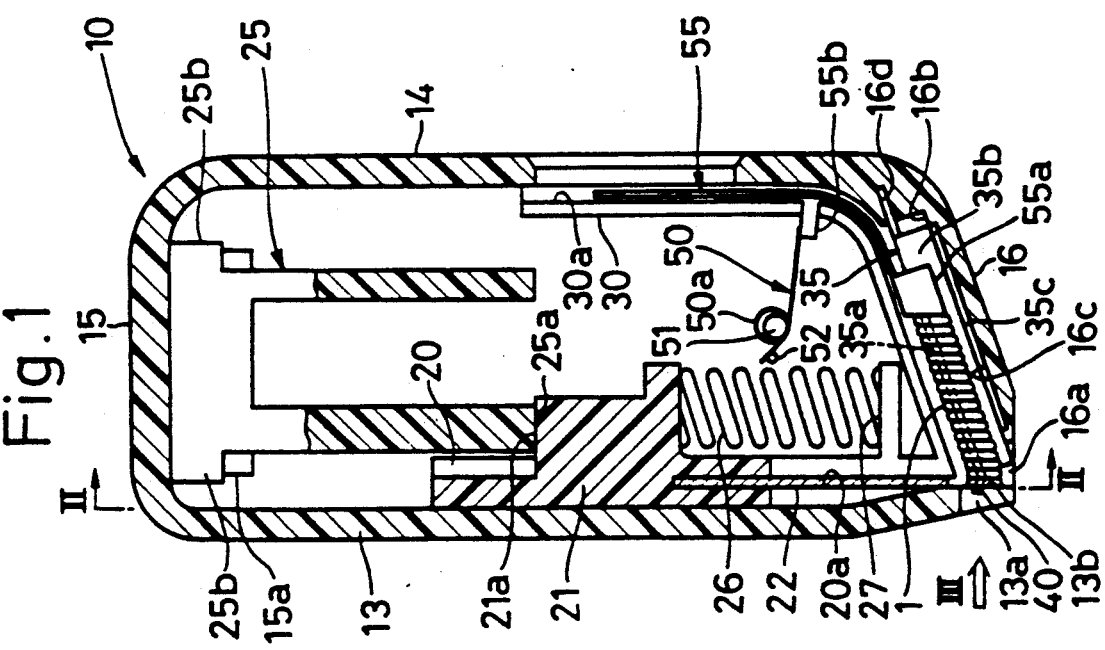

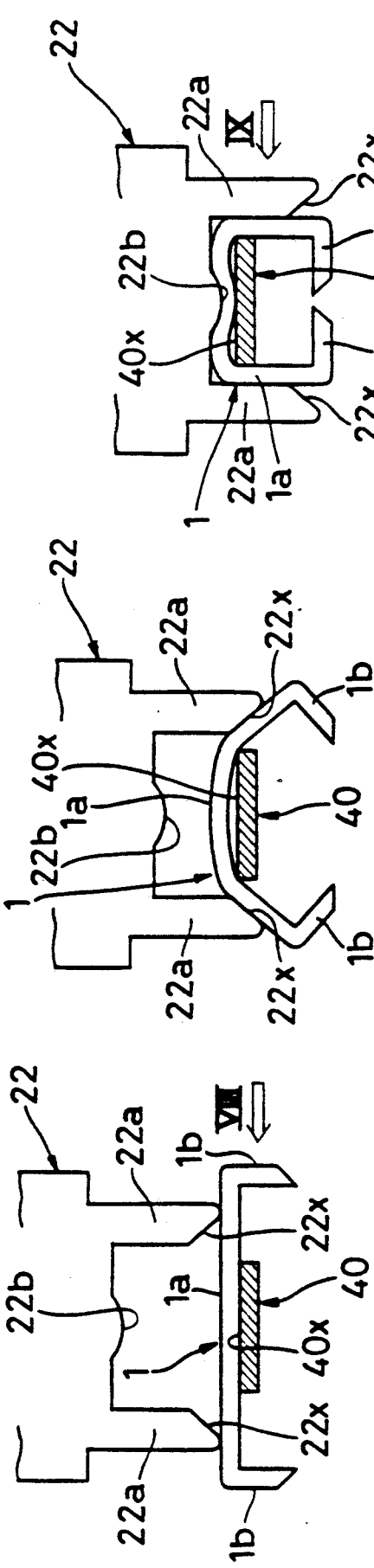

MEDICAL STAPLER

BACKGROUND OF THE INVENTION

This invention relates to a medical or surgical stapler.

As disclosed in U.S. Pat. No. 4,411,378, a medical stapler includes a casing having an opening. The inner surfaces of those portions of the casing disposed immediately adjacent respectively to the opposite side edges of the opening serve respectively as retaining surfaces for a staple. First and second guide members, extending respectively along straight lines intersecting each other, are provided within the casing. A ram is slidably supported on the first guide member. An anvil extends from the distal end of the second guide member. The anvil is disposed in the vicinity of the opening of the casing, and is disposed in a path of movement of the ram. The ram has first shaping surfaces at its distal end, and the anvil has a second shaping surface disposed in opposed relation to the ram. The second shaping surface of the anvil is disposed perpendicular to the path of movement of the ram. A number of staples are slidably supported on the second guide member, and are arranged in contiguous relation to one another in the direction of the length of the second guide member. Each of the staples has a crown portion, and a pair of legs formed respectively at the opposite ends of the crown portion. A spring, provided within the casing, pushes a rearmost one of a number of staples, supported on the second guide member, to urge these staples toward the anvil. When an operating member, mounted on the casing, is operated to advance the ram, the foremost staple is shaped through the cooperation of the ram with the anvil in such a manner that the pair of legs thereof are moved toward each other, and during this shaping operation, a required portion of a patient is sutured.

In the medical stapler of the above U.S. Patent, during the shaping of the foremost staple, the crown portion thereof rolls on the second shaping surface of the anvil, and therefore there is a possibility that a satisfactory suturing may not be achieved. More specifically, the anvil is fixedly mounted on the casing, but the ram is supported on the first guide member with a slight play in a direction perpendicular to the path of movement of the ram in order to ensure a smooth sliding movement of the ram. During the shaping of the foremost staple, the upper portion of the crown portion thereof is contacted with the first shaping surfaces of the ram under a large force, whereas the lower portion of the crown portion is contacted with the second shaping surface of the anvil under a large force. The crown portion of the foremost staple receives the force of the above spring via the crown portions of the subsequent staples; however, since the legs of the foremost staple are abutted against the retaining surfaces of the casing, the crown portion is prevented from rolling. When the shaping of the foremost staple further proceeds, so that the legs of the foremost staple are disengaged from the retaining surfaces, the crown portion may roll on the second shaping surface, because the crown portion of the foremost staple is urged by the crown portions of the subsequent staples, and the ram is moved by an amount corresponding to the above play.

U.S. Pat. No. 4,261,244 discloses a stapler in which a V-shaped groove, which is disposed perpendicular to a path of movement of a ram and extends parallel to a crown portion of each staple, is formed in each of first shaping surfaces of the ram. Each staple has a polygonal cross-section. When the foremost staple is to be shaped, the upper portion of the crown portion thereof is received in the V-shaped grooves. In this conventional stapler, the rolling of the foremost staple can be prevented, but the manufacturing cost of the staple having a polygonal cross-section is high. If staples of a circular cross-section are used, there is a possibility that the upper portion of the crown portion of the foremost staple may slip in the V-shaped grooves, thereby inviting a possibility that the crown portion may roll on a second shaping surface of an anvil.

U.S. Pat. Nos. 4,582,237 and 4,662,555 disclose staplers in which a groove for receiving an upper portion of a crown portion of a foremost staple is formed in each of first shaping surfaces of a ram.

Some of the inventors of the present invention earlier developed a stapler disclosed in U.S. Pat. No. 5,022,579, and this stapler resembles the stapler of the present invention, but does not have the features of the present invention.

SUMMARY OF THE INVENTION

It is an object of this invention to provide a medical stapler which can shape a staple satisfactorily.

According to the present invention, there is provided a medical stapler comprising:

(a) a casing having an opening;

(b) first guide means provided within the casing and extending generally linearly;

(c) a ram supported on the first guide means for sliding movement therealong, the ram having first shaping surfaces at its distal end;

(d) an operating member mounted on the casing so as to advance the ram;

(e) second guide means provided within the casing and extending in a direction intersecting a path of movement of the ram, a plurality of staples being slidably supported on the second guide means and arranged in contiguous relation to one another in a direction of a length of the second guide means, and each of the staples having a crown portion, and a pair of legs extending angularly from opposite ends of the crown portion, respectively;

(f) an anvil extending from a distal end of the second guide means, the anvil being disposed in the vicinity of the opening of the casing and disposed in the path of movement of the ram, the anvil having a second shaping surface disposed in opposed relation to the ram, and the second shaping surface being inclined relative to the path of movement of the ram in such a manner as to approach the ram progressively toward a distal end of the second shaping surface;

(g) urging means for urging the plurality of staples, supported by the second guide means, toward the anvil; and (h) retaining means provided in the vicinity of the opening of the casing so as to retain the pair of legs of a foremost one of the plurality of staples to thereby place the crown portion thereof on the anvil, the foremost staple being shaped through the cooperation of the advancing ram with the anvil in such a manner that the pair of legs thereof are moved toward each other, and upon the shaping of the foremost staple, the foremost staple being brought out of retaining engagement with the retaining means.

BRIEF DESCRIPTION OF THE DRAWINGS

FIG. 1 is a vertical cross-sectional view of a medical stapler provided in accordance with the present invention;

FIG. 2 is a cross-sectional view taken along the line II—II of FIG. 1;

FIGS. 5 to 7 are views showing the sequence of the shaping operation of the staple;

FIG. 8 is an enlarged side-elevational view of the staple as seen in a direction VIII of FIG. 5; and FIG. 9 is an enlarged side-elevational view of the staple as seen in a direction IX of FIG. 7.

DESCRIPTION OF THE PREFERRED EMBODIMENT

Figure 3:
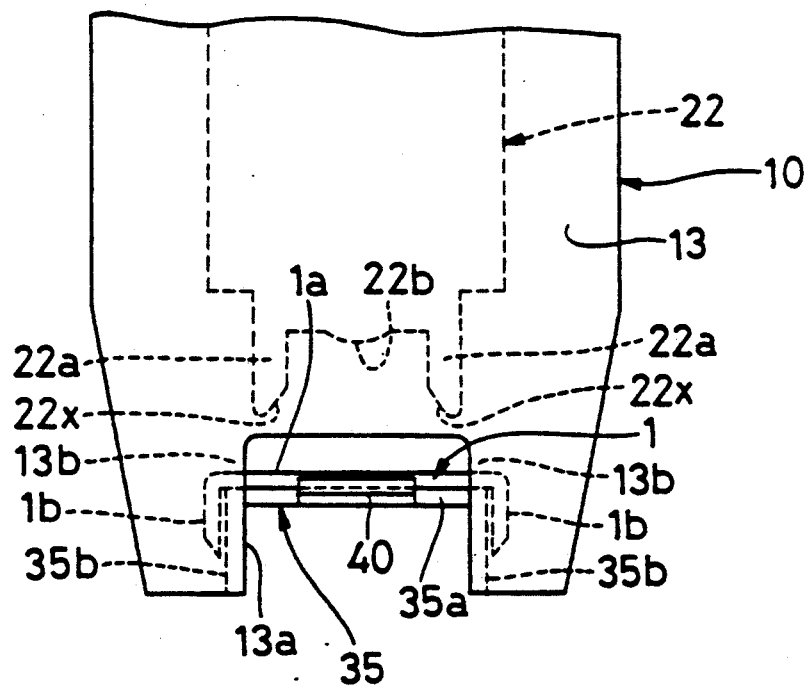
FIG. 3 is an enlarged front-elevational view of a portion of the stapler as seen in a direction III of FIG. 1.
Figure 4:
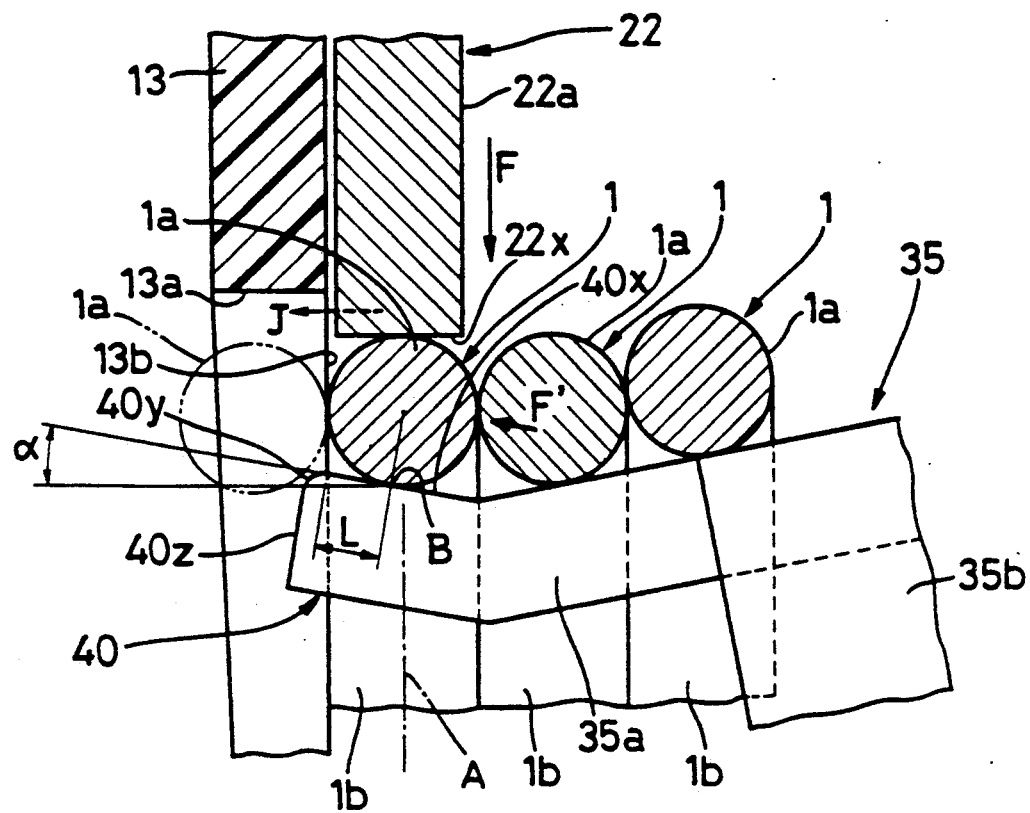
FIG. 4 is an enlarged cross-sectional view of a lower end portion of the stapler of FIG. 1.

A preferred embodiment of the present invention will now be described with reference to the drawings. FIGS. 1 and 2 show a disposable stapler. This stapler comprises an elongate hollow casing 10 made of a resin. The casing 10 has a pair of opposed flat side walls 11 and 12 extending longitudinally in generally parallel relation to each other, and also has a pair of opposed side walls 13 and 14, an upper wall 15, and a lower wall 16 which perpendicularly intersect the side walls 11 and 12. The side walls 13 and 14 extend longitudinally of the casing 10 in generally parallel relation to each other. The lower wall 16 is inclined with respect to the longitudinal axis of the casing 10. An opening 13a is formed at the lower end portion of the side wall 13, and this opening 13a has a rectangular shape as shown in FIG. 3. As shown in FIGS. 1, 3 and 4, the inner surfaces of those portions of the side wall 13 disposed immediately adjacent respectively to the opposite side edges of the opening 13a serve respectively as retaining surfaces (retaining means) 13b for a staple 1 (later described). An opening 16a continuous with the opening 13a is also formed at one end portion of the lower wall 16 close to the side wall 13.

A pair of parallel spaced guide portions (first guide means) 20 are formed integrally on the inner surface of the side wall 13, and extend longitudinally of the casing 10. In FIG. 1, only one of the two guide portions 20 is shown. A slider 21 is received between the pair of guide portions 20 for sliding movement therealong. A ram 22 made of a metal plate is fixedly secured at its upper end portion to the lower end portion of the slider 21. The ram 22 is slidably received in grooves 20a, formed respectively in the opposed surfaces of the guide portions 20, with a slight play. As shown in FIGS. 2 and 3, the ram 22 has a pair of opposed main projections 22a formed at its lower end and projected downwardly, and a downwardly-projecting sub-projection 22b formed on the lower end thereof and disposed between the main projections 22a. The length of projecting of the sub-projection 22b is far shorter than that of the main projection 22a. The lower end surface of each main projection 22a serves as a first shaping surface 22x. The first shaping surfaces 22x are parallel to a certain straight line. This straight line is perpendicular to the path of movement of the ram 22, and is perpendicular to a crown portion 1a (later described) of the staple 1.

As shown in FIGS. 1 and 2, a bearing 15a is formed on the casing 10 adjacent to the upper end thereof, and a shaft portion 25b of an operating lever (operating member) 25 which is formed at the proximal end of this lever is pivotally supported by the bearing 15a. The operating lever 25 is extended outwardly from the casing 10 through an opening 12a formed through the side wall 12. A cam surface 25a is formed on the operating lever 25. When the operating lever 25 is pivotally moved toward the casing 10, the cam surface 25a urges a cam follower 21a, formed integrally with the slider 21, to move the slider 21 downward, thereby moving the ram 22 downward.

The slider 21 is urged upward by a return spring 26, so that the cam follower 21a is always held against the cam surface 25a of the operating lever 25. The return spring 26 acts between the slider 21 and a spring seat 27 formed integrally with the casing 10.

As shown in FIG. 1, a pair of projections 30 (only one of which is shown in FIG. 1) are formed integrally on the inner surfaces of the side walls 11 and 12 of the casing 10. More specifically, the pair of projections 30 extend from a point generally midway between the opposite ends of the side wall 14 to the end of the lower surface 16 remote from the side wall 14. Grooves 30a are formed respectively in the opposed surfaces of those portions of the projections 30 extending along the side wall 14. A recess 16b is formed in the inner surface of the lower wall 16 of the casing 10, and extends along the lower wall 16. One end of the recess 16b is continuous with the grooves 30a, and the other end thereof is continuous with the openings 13a and 16a of the casing 10.

A guide member (second guide means) 35 made of a metal plate is fixedly received in the recess 16b. The guide member 35 extends along the lower wall 16, that is, in a direction intersecting the path of movement of the ram 22. As shown in FIG. 3, the guide member 35 has a flat base plate portion 35a, and a pair of side plate portions 35b formed respectively at the lateral edges of the base plate portion 35a. As shown only in FIG. 1, the guide member 35 further has a pair of bottom plate portions 35c extending respectively from the lower edges of the pair of side plate portions 35b away from each other, the bottom plate portions 35c longitudinally extending parallel to the base plate portion 35a. The pair of bottom plate portions 35c are received respectively in a shallow auxiliary recess 16c formed in the bottom surface of the recess 16b. The rear end portion of the base plate portion 35a is received in a groove 16d formed in a rear side wall of the recess 16b.

An anvil 40 is formed integrally with and extends from the front end of the base plate portion 35a of the guide member 35 toward the opening 13a. The anvil 40 is disposed in the path of movement of the ram 22. As best shown in FIG. 4, the anvil 40 has a second shaping surface 40x which is flat and disposed in opposed relation to the ram 22, a flat distal end surface 40z, and a curved surface 40y interconnecting the surfaces 40x and 40z. The curved surface 40y is the result of a shear droop produced when the guide member 35 and the anvil 40 are formed by pressing. As best shown in FIGS. 3 and 5, the sub-projection 22b of the ram 22 is disposed right above the anvil 40, and the distance between the pair of main projections 22a is larger than the width of the anvil 40 by an amount slightly larger than the double of the diameter of the crown portion 1a of the staple 1.

A number of staples 1 are supported on the guide member 35, and are arranged in contiguous relation to one another in the direction of the length of the guide member 35. Each staple 1 is formed by pressing a stainless steel wire of a circular cross-section having a predetermined length and a diameter of about 0.5 mm. As best shown in FIGS. 3 and 5, the staple 1 has the straight crown portion 1a, and a pair of legs 1b extending perpendicularly from the opposite ends of the crown portion 1a, respectively. The distal end of each leg 1b is cut obliquely to provide a piercing ability. As shown in FIG. 8, the axis of the crown portion 1a and the axes of the two legs 1b are disposed in a common plane A. As shown in FIG. 3, each staple 1 is supported on the guide member 35 in straddling relation thereto. More specifically, the crown portion 1a of the staple 1 is borne by the base plate portion 35a of the guide member 35, and the pair of legs 1b are disposed outwardly of the pair of side plate portions 35b of the guide member 35 in slightly spaced, opposed relation thereto.

As shown in FIG. 1, a number of staples 1 are urged by a spring 50 via a push member 55. More specifically, the push member 55 comprises an elongate plate so flexible as to be bent. The lateral edges of the push member 55 are slidably received respectively in the grooves 30a of the projections 30. An abutment portion 55a of an inverted U-shaped cross-section is formed at the distal end of the push member 55, and this abutment portion 55a is slidably supported on the guide member 35 in straddling relation thereto. A projection 55b is formed on the push member 55 intermediate the opposite ends thereof. The spring 50 has a coiled portion 50a which is supported on a projection 51 formed on the casing 10. One end of the spring 50 is retained by a projection 52 formed on the casing 10, and the other end of the spring 50 is firmly held against the projection 55b of the push member 55 under the resilient force of the spring 50, thereby urging the push member 55 downward. Therefore, the abutment portion 55a of the push member 55 is firmly abutted against the rearmost staple 1 to urge a number of staples 1 toward the anvil 40. As a result, the pair of legs 1b of the foremost staple 1 are held against the retaining surfaces 13b of the casing 10, respectively, and the crown portion 1a thereof is placed on the anvil 40. The common plane A in which the foremost staple 1 is disposed is parallel to the path of movement of the ram 22, and also is parallel to the retaining surfaces 13b.

Next, features of the present invention related to the anvil 40 will now be described. As shown in FIG. 4, the second shaping surface 40x of the anvil 40 is inclined relative to the path of movement of the ram 22 in such a manner as to approach the ram 22 progressively toward the distal end of the second shaping surface 40x. The angle of inclination of the second shaping surface 40x with respect to a plane perpendicular to the path of movement of the ram 22 is indicated by "α" in FIG. 4, and is about 2° in this embodiment. This inclination angle is shown in an exaggerated manner in FIGS. 1 and 4.

The anvil 40 is shorter than that of conventional staplers. More specifically, the length L from a point B of contact between the second shaping surface 40x and the crown portion 1a of the foremost staple 1 in the retained condition to the distal end of the second shaping surface 40x is less than the diameter of the crown portion 1a of the staple 1. Preferably, the length L is larger than ¼ of the diameter of the crown portion 1a of the staple 1, and is smaller than ¾ of this diameter. In this embodiment, the length L is almost equal to the radius of the crown portion 1a of the staple 1, and strictly the length L is slightly smaller than the radius of the crown portion 1a of the staple 1.

In the medical stapler of the above construction, when the ram 22 is moved downward by operating the operating member 25, the first shaping surfaces 22x of the main projections 22a are brought into engagement with the crown portion 1a of the foremost staple 1, as shown in FIGS. 4 and 5. When the ram 22 further moves downward, the opposite end portions of the crown portion 1a are bent through the cooperation of the pair of first shaping surfaces 20x with the opposite ends of the second shaping surface 40x, as shown in FIG. 6. When the ram 22 further moves downward, the opposite end portions of the crown portion 1a is bent generally perpendicularly to the central portion thereof, as shown in FIG. 7, thus finishing the shaping operation. During the process of bending the crown portion 1a in this manner, the distal ends of the pair of legs 1b are moved toward each other, so that they pierce into that portion of a patient to be sutured, and at the time when the shaping (bending) of the foremost staple 1 is completed, the staple 1 has a generally rectangular shape. By doing so, the suturing of that portion of the patient is completed.

During the shaping of the foremost staple 1, the crown portion 1a of the foremost staple 1 receives, through the crown portions 1a of the subsequent staples 1, a force F' (FIG. 4) which results from the resilient force of the spring 50 and acts parallel to the second shaping surface 40x of the anvil 40. When the legs 1b of the foremost staple 1 are held in contact with the retaining surfaces 13b, respectively, the foremost staple 1 is prevented from rolling. When the shaping of the foremost staple 1 proceeds as shown in FIG. 6, the legs 1b thereof are moved out of contact with the retaining surfaces 13b, respectively. At this time, assuming that the anvil 40 is disposed perpendicular to the path of movement of the ram 22 as is the case with the prior art, the crown portion 1a of the foremost staple 1 would be rolled toward the opening 13a by the above force F', because the ram 22 is movable in a direction (indicated by arrow J in FIG. 4) perpendicular to the path of movement of the ram 22 by an amount equal to the play.

In the present invention, however, the anvil 40 is inclined with respect to the path of movement of the ram 22, and therefore even if the legs 1b of the foremost staple 1 are disengaged respectively from the retaining surfaces 13b during the shaping of this staple, the rolling of the crown portion 1a thereof can be prevented. More specifically, a shaping force F of the ram 22 acting parallel to the path of movement of the ram 22 contains a component $F \sin\alpha$ acting parallel to the second shaping surface 40x of the anvil 40. This force $F \sin\alpha$ acts in a direction opposite to the direction of acting of the above force F', and therefore if the inclination angle α is so determined that these two forces are equal to each other, the force acting on the crown portion 1a in parallel relation to the second shaping surface 40x can be reduced to zero, thereby preventing the rolling of the crown portion 1a. By doing so, the staple 1 can be shaped in such a manner that the common plane A in which the staple 1 is disposed is kept parallel to the path of movement of the ram 22. As a result, as shown in FIG. 9, the axes of the crown portion 1a and legs 1b of the shaped staple 1 can be disposed in the common plane A, and the suturing can be carried out satisfactorily.

The component Fsinα of the shaping force F of the ram 22 which acts in the direction parallel to the second shaping surface 40x of the anvil 40 may not be completely equal to the force F' which is produced by the resilient force of the spring 50 and is parallel to the second shaping surface 40x. In this case, if the difference between these two forces, that is, the force actually acting on the crown portion 1a of the staple 1 in parallel relation to the second shaping surface 40x, is sufficiently smaller than that produced with the conventional staplers, the rolling of the crown portion 1a can be prevented.

The rolling of the foremost staple 1 does not occur as described above, and therefore even if the anvil 40, as well as the length L from the point B of contact between the second shaping surface 40x and the foremost staple 1 to the distal end of this surface 40x, is shorter as compared with the conventional staplers, there is not encountered a disadvantage that the crown portion 1a is disengaged from the anvil 40 during the shaping operation.

When the operating lever 25 is released after the above shaping of the foremost stapler 1, the ram 22 is retracted upward. At this time, the foremost staple 1 is pushed by the next staple 1 toward the opening 13a until the legs 1b of the next staple 1 is brought into engagement with the retaining surfaces 13b, respectively, so that the foremost staple 1 reaches a position indicated in phantom in FIG. 4. Therefore, thereafter, merely by moving the stapler upward, the staple 1 attached to the sutured portion of the patient can be disengaged from the stapler, because the crown portion 1a of the foremost staple 1 disposed in the position indicated in phantom is spaced from the second shaping surface 40x, and therefore when the stapler is moved upward, the crown portion 1a of the staple 1 will not interfere with the anvil 40. Incidentally, in the conventional stapler having a long anvil, in order to disengage the anvil from the crown portion of the staple, the stapler must be moved in the direction of the length of the anvil 40, that is, in the right-hand direction in FIG. 4. Therefore, the stapler of this embodiment can carry out the suturing operation more easily, as compared with the conventional stapler.

If the length L from the point B of contact between the second shaping surface 40x and the stapler 1 to the distal end of this surface 40x is longer than that in the embodiment of FIG. 4 and is less than the diameter of the staple 1, the crown portion 1a of the shaped foremost staple 1 pushed by the next staple 1 is held in contact with the curved surface 40y of the anvil 40. In this case, when the stapler is moved upward, the crown portion 1a of the foremost staple 1 slides over the curved surface 40y to be disengaged from the anvil 40 in response to the upward movement of the anvil 40.

After the opposite end portions of the crown portion 1a of the foremost staple 1 are bent respectively by the main projections 22a of the ram 22, these opposite end portions tend to slightly move away from each other due to a spring back effect. Therefore, the opposite end portions of the crown portion 1a tend to resiliently contact the main projections 22a, respectively. In this embodiment, however, this spring back can be canceled. More specifically, during the shaping operation, the central portion of the crown portion 1a slightly floats off the second shaping surface 40x of the anvil 40, as shown in FIG. 6. Then, immediately before the completion (FIG. 7) of the shaping of the staple 1, the floating central portion of the crown portion 1a is bent or curved downward by the sub-projection 22b of the ram 22. Although this deformation of the central portion of the crown portion 1a is slight, this is shown in an exaggerated manner in FIG. 7 for illustration purposes. The spring back of the thus downwardly-curved portion serves to move the opposite end portions of the crown portion 1a toward each other. Therefore, the spring back due to the shaping by the main projections 22a and the spring back due to the shaping by the sub-projection 22b cancel each other. As a result, the friction between each of the opposite end portions of the crown portion 1a and its corresponding main projection 22a is reduced, and when the ram 22 is moved upward after the shaping operation is finished, the staple 1 is prevented from moving together with the ram 22, so that damage to the sutured portion of the patient by the upward movement of the staple can be prevented.

The present invention is not limited to the above embodiment, and various modifications can be made. For example, a V-shaped groove for receiving the upper portion of the crown portion of the staple may be formed in each of the first shaping surfaces of the ram. The distal end of the ram may have any suitable shape corresponding to the shape of the staple to be used.

What is claimed is:

1. A medical stapler comprising:
   (a) a casing having an opening;
   (b) first guide means for guiding a ram provided within said casing and extending generally linearly;
   (c) a ram supported on said first guide means for sliding movement therealong, said ram having first shaping surfaces disposed in opposed relation to an anvil;
   (d) an operating member mounted on said casing so as to advance said ram;
   (e) second guide means for guiding staples provided within said casing and extending in a direction intersecting a path of movement of said ram, a plurality of staples being slidably supported on said second guide means and arranged in contiguous relation to one another in a direction of a length of said second guide means, and each of said staples having a crown portion, and a pair of legs extending angularly from opposite ends of said crown portion, respectively;
   (f) said anvil extending from a distal end of said second guide means, said anvil being disposed in the vicinity of said opening of said casing and disposed in the path of movement of said ram, said anvil having a second shaping surface disposed in opposed relation to said ram, said second shaping surface having a distal end in the direction of the end of said second guide means, and said second shaping surface being inclined relative to the path of movement of said ram so that a distance in a direction of the path of movement of said ram between said first and second shaping surfaces progressively decreases toward said distal end of said second shaping surface;
   (g) urging means for urging said plurality of staples, supported by said second guide means, toward said anvil; and (h) retaining means provided in the vicinity of said opening of said casing so as to retain the pair of legs of a foremost one of said plurality of staples to thereby place the crown portion thereof on said anvil, the foremost staple being shaped through the cooperation of the advancing ram with said anvil in such a manner that the pair of legs thereof are moved toward each other, and upon the shaping of the foremost staple, the foremost staple being brought out of retaining engagement with said retaining means.

2. A medical stapler according to claim 1, in which said second shaping surface of said anvil is flat, the distance from a point of contact between the crown portion of the foremost staple retained by said retaining means and said second shaping surface to the distal end of said second shaping surface is smaller than the diameter of the crown portion of the staple.

3. A medical stapler according to claim 1, in which said ram has a pair of main projections and a sub-projection which are formed at the distal end of said ram and are directed away from a proximal end of said ram, the distance between said pair of main projections being larger than the width of said anvil, said anvil being disposed between said pair of main projections in the advanced position of said ram, and said sub-projection being shorter than said pair of main projections, and being provided between said pair of main projections in opposed relation to said anvil.

* * * * *